United States Patent
Hakki et al.

[11] Patent Number: 5,609,583
[45] Date of Patent: Mar. 11, 1997

[54] COLLAPSIBLE CATHETER

[76] Inventors: A-Hamid I. Hakki; Said I. Hakky, both of 8547 Merrimoor Blvd., E., Largo, Fla. 34647-3145

[21] Appl. No.: 531,476

[22] Filed: Sep. 21, 1995

[51] Int. Cl.$^6$ ............................................. A61M 25/00
[52] U.S. Cl. ............................. 604/282; 604/96; 606/194
[58] Field of Search ................ 604/96–103, 280, 604/282; 606/192, 194; 600/114, 115, 121, 123

[56] References Cited

U.S. PATENT DOCUMENTS 5,522,801   6/1996   Wang .................................... 604/96

*Primary Examiner*—Corrine M. McDermott
*Attorney, Agent, or Firm*—John Lezdey and Assoc.

[57] ABSTRACT

A collapsible catheter is provided for irrigation or aspiration of the urinary bladder with fluid. The catheter consists of a pair of telescoping collapsible hollow elastomeric tubes which form an opening at the proximal end. A drainage opening is provided at the distal end. The catheter is stiffened by inserting fluid between the tubes through a valve. A balloon is provided to hold the catheter in place in a patient.

8 Claims, 1 Drawing Sheet

COLLAPSIBLE CATHETER

FIELD OF THE INVENTION

The present invention relates to a surgical device and method for draining or feeding a biological system and in particular a collapsible indwelling catheter is provided for draining or aspirating the urinary bladder.

BACKGROUND OF THE INVENTION

A urinary bladder tube is used on patients who are unable to urinate. There are many causes of the inability to urinate. Frequently, surgery or other invasive procedures produce such an effect. Generally, the origin of such a condition differs with age and gender. For example, the inability to urinate in men is commonly caused by a blockage of the urethra passageway by an enlargening prostate. In females, the condition may occur after delivery of a baby. And, in small children, a congenital abnormality obstructing the bladder neck or urethra can produce the condition.

After major surgery, it is advantageous to continuously drain the bladder. Continuous drainage of the bladder is also preferred where medical conditions dictate the necessity of monitoring a patient's urine output. It is well known that close measurement of urine output provides a direct correlation to kidney functions and careful monitoring allows one to identify and prevent kidney failure.

It is important to drain the bladder by an indwelling catheter after prostate or bladder surgery. An indwelling Foley type catheter is usually the catheter of choice. U.S. Pat. No. 5,300,022 to Klapper et al and incorporated herein, shows an improvement over the Foley catheter by providing a second lumen for continuous delivery of a sterile irrigating solution directly into the bladder, and preventing any mixture with the main drainage lumen, thus avoiding any reintroduction of harmful bacteria into the bladder during irrigation.

U.S. Pat. No. 4,701,162 issued to Rosenberg and incorporated herein, shows a Foley catheter with two lumens, one for drainage and one for inflation of the balloon. Having separate lumens for drainage and inflation is common in the prior art. U.S. Pat. No. 5,098,379, which is incorporated herein by reference, discloses a Foley catheter having a balloon portion and a lubricated resilient sleeve. U.S. Pat. No. 5,269,770, which is incorporated herein by reference, shows a dual lumen system and balloon Foley catheter for releasing a bactericidal agent. Similarly, U.S. Pat. No. 5,269,755 which is incorporated therein by reference, shows a Foley urinary catheter with a dual membrane delivery system that allows bactericidal agents to diffuse into the urinary tract.

One thing is clear in the prior art of Foley urinary catheters: none of them teach a collapsible device.

An indwelling catheter drains the bladder and diverts the urine from the wound. Moreover, the bladder can be either continuously irrigated with a three way Foley catheter or hand irrigated at discrete moments when desired. In the three way catheter, one port is connected to a large fluid reservoir and the other port is used for drainage of the returned fluid. The speed of irrigation can be controlled by different mechanisms or different pumps.

In certain patients the bladder must be drained for many years, as in patients with spinal cord lesions. If the bladder is not drained, the pressure inside it will build up and obstruct the kidneys. Continuous kidney obstruction could end in renal failure and death in only a few weeks. Furthermore, the catheter is used to clear blockages and constrictions of the urinary tract.

Therefore, the use of indwelling catheter is very important and could be life saving.

However, there are many serious draw backs to the stiff indwelling catheter. First, it is painful and certain patients cannot tolerate the catheter. Second, a stiff hollow indwelling catheter invites micro-organisms to invade the bladder and kidneys which may cause a serious infection. Third, for patients who are unable to tolerate the stiff catheter, a hole in the bladder must be created to drain the bladder directly through the anterior abdominal wall. This is a serious procedure and exposes the patient to unnecessary risks of other complications.

Thus, it would be ideal if a Foley catheter was stiff enough to be introduced, but collapsed after insertion. The urethra is naturally in a state of collapse at rest. The present invention The pain or will mimic the urethra's physiological status.

reduced. In discomfort from an indwelling catheter will be infection is addition, the incidence of bladder or kidney minimized.

SUMMARY OF THE INVENTION

The present invention relates to a catheter for insertion into a patient which is aimed at reducing the discomfiture experienced with conventional indwelling catheters. The catheter of the invention comprises a pair of substantially collapsible elongated elastomeric telescoping tubes which are joined together and have an opening at a proximal end and have at least one opening for fluid drainage into the inner tube. The tubes are joined together and closed at the distal end. A valve means is provided about the proximal end to permit fluid entrance between the tubes so as to stiffen the catheter for insertion into the patient and to remove the fluid so as to cause the catheter to collapse.

Advantageously, the tubes are joined or bonded together so as to be reinforced at the proximal end, the distal end and about the drainage opening. Preferably, a balloon means is provided near the distal end to maintain the catheter within the patient after its collapse. A small hollow tube connects the balloon to a valve system located near the open proximal end.

Advantageously, the tubes are joined or bonded at different points along their length. The bonding or joining of the tubes and their reinforcement at the openings or at the distal end can be by use of adhesives, fusion bonding of the tubes alone or with a fusible polymeric material. In the device, the tubes are thin enough to keep them in a state of collapse at rest. The collapsible tubes are open at one end, that is, the proximal end to permit access into the inner tube. The open end preferably has a valve means which allows passage of fluid into and out of the tube.

There are one or more holes, at the distal end of the catheter, which is the end that connects to the bladder. A circular hollow tube or a thickener portion can be used to reinforce the open end of the catheter tube, which is the end that can be connected to a calibrated urine bag. The reinforcement prevents collapse of the open end and facilitates the insertion of the tube for connection to a urine bag.

In a three way injection system, an extra hollow tube can be added at the proximal end of the catheter and connected to a reservoir for irrigation. This tube does not need to be reinforced.

A method is also provided for irrigating and aspirating the urinary tract using a device as the present invention describes herein.

OBJECT OF THE INVENTION

Accordingly, it is the general object of this invention to provide a collapsible catheter that mimics the urethra in every respect, thus overcoming the disadvantages of the prior art.

It is a further object of the invention to provide a catheter and method of aspirating the bladder after surgery which can be used with less discomfiture to the patient.

It is a further object of this invention to provide a catheter and method of irrigating the bladder for certain urological conditions.

It is a further object of this invention to provide a catheter that advantageously can be at least partially stiffened or flaccid when desired, thus minimizing the incidence of infection and reducing the pain or discomfort the patient experiences during the period that the catheter is left indwelling.

It is a further object of this invention to provide a collapsible catheter that advantageously can be stiff or flaccid when desired, thus minimizing the incidence of infection and reducing the pain or discomfort the patient experiences during the period when the tube is left indwelling.

DETAILED DESCRIPTION OF THE PREFERRED EMBODIMENTS

Figure 1:
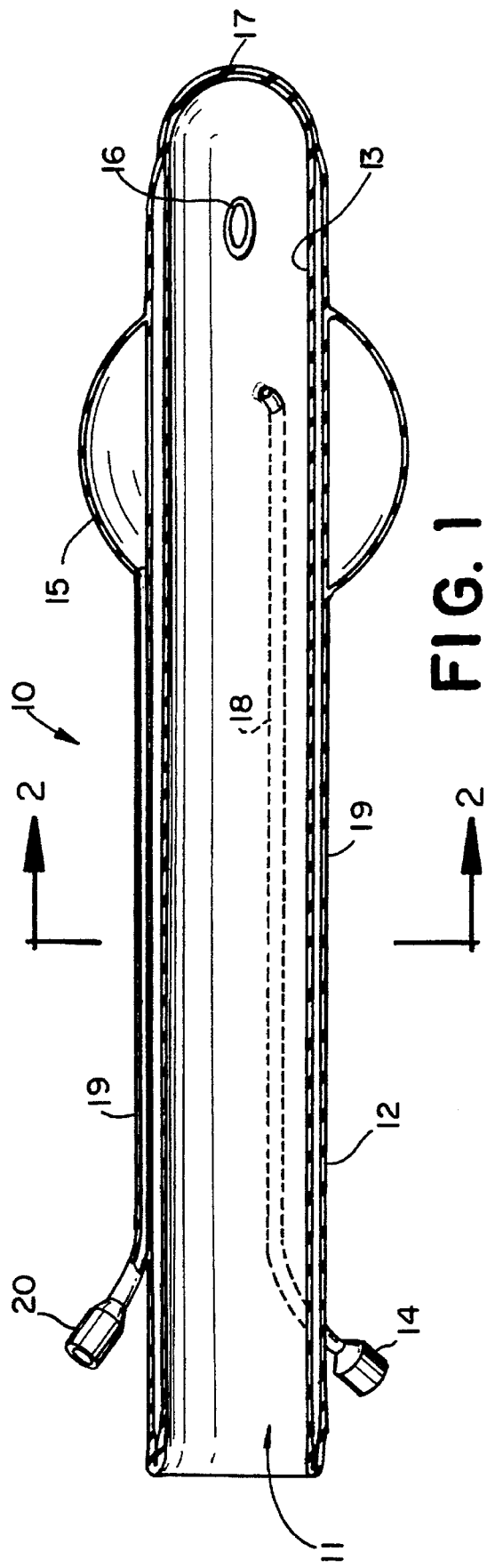
FIG. 1 is a perspective view of the collapsible catheter of the invention.

Although specific terms are used in the following description for the sake of clarity, these terms are intended to refer only to the particular structure of the invention selected for illustration in the drawings and are not intended to define or limit the scope of the invention.

As shown in FIG. 1, the catheter 10 of the invention is formed by a first collapsible hollow tube 13 which is within a second collapsible hollow tube 12. The tubes 12,13 are joined or bonded together so as to have an opening 11 at the proximal end of the catheter 10. The tubes 12,13 are further joined or bonded at the distal end 17 and at various points 21 along the length.

The outside circumference of the outer tube 12 is slightly larger than the outside circumference of tube 13, generally, about 0.33 mm larger. The outside diameter of tube 12 is generally about 1.6 to 10 mm and the length of the tube 12 can vary between about 13 to 17 inches (8387.08 to 10967.72 mm).

There are one or more reinforced openings or holes 16, preferably two or three, located at the distal end of catheter 10 which is the end that connects into the bladder. The holes 16 are advantageously six to eight millimeters in diameter. The distal tip 17 is preferably thickened to aid in insertion into the bladder.

The open end 11 of the catheter 10 is the end that can be connected to a calibrated urine bag. This end 11 can be thickened or reinforced with a circular hollow tube or a valve to prevent collapse of the open end and facilitate the connection of the catheter 10 to a urine bag (not shown).

To prevent the catheter 10 from slipping out of the urinary bladder an inflatable balloon 15 can be provided near the distal end as shown in FIG. 1. The balloon 15 may be inflated through the hollow tube or channel 19 which runs along wall of the catheter 10 to a valve system 20. The tube 19 can be on the outside wall or between the tubes 12,13.

In a three way irrigation system an extra hollow tube may be added to the catheter 10. This tube may be connected to a reservoir of fluid for irrigation.

The collapsible tubes 12,13 may be made from medically approved silicone rubber, latex rubber or any other suitable medically approved elastomer. The distal end 17 is preferably thickened about 1 to 2 cm so as to provide sufficient stiffness to prevent collapse during drainage. The proximal end which has the opening 11 preferably has a thickness of about 2–3 cm in length to prevent collapse.

The valve systems 14 and 20 may be one, two or three ways. The balloon member 15 is attached to the periphery of the catheter 10. The balloon 15 is at least partially inflated to prevent the catheter 10 from slipping out of the urinary bladder. The balloon 15 is attached to the outside of the catheter 10 and is connected to a small hollow tube 19 of the valve system 20 located near the proximal end. The balloon can be filled with air or fluid through use of a syringe. The balloon can be fully or partially inflated to support the sides of the tube.

Figure 2:
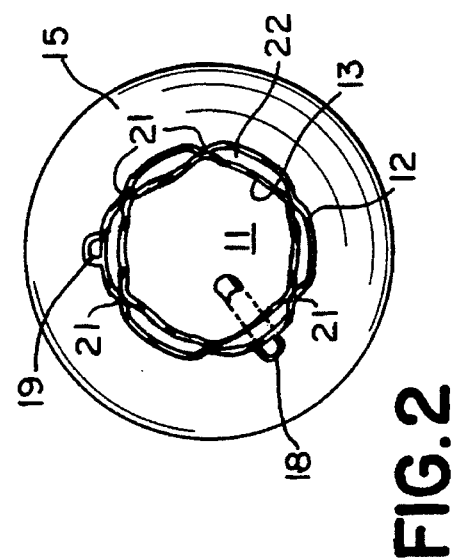
FIG. 2 is a cross-section of the collapsible catheter of FIG. 1 taken along line 2—2.

As shown in FIG. 2, the bonded points 21 are spaced so that the space 22 between the tubes 12,13 is continuous along the length whereby fluid which is inserted through the valve 14 and into space 22 will pressurize and completely stiffen the catheter 10 for insertion into a patient. The degree of collapse can be controlled by removal of fluid from between the space 21.

The present invention will mimic the physiological status of the urethra in every respect. In the event of a three way urethral catheter, the fluid will distend the hollow non-reinforced tube when the fluid is turned on. If the fluid is turned off, the infusion or irrigating hollow tube will collapse.

In certain difficult cases, the balloon is injected through the valve 14 with fluid from a syringe until the catheter 10 is stiff enough to be threaded into the bladder. The balloon 15 of the catheter is then further inflated with fluid to prevent the catheter from slipping out of the bladder. The balloon 15 can then be deflated in the manner just described.

In the method for draining the urinary bladder, the catheter is stiffened by inserting fluid between the tubes 12,13, i.e. spaces 22, with a syringe through valve system 14. The stiffened urethral catheter is well lubricated and passed urethrally into the bladder. Once the urethral catheter is in position, as noted by the return of urine, the balloon 15 at the distal end of the catheter is inflated. After the catheter 10 is secured in the urinary bladder, the fluid from between the tubes 12,13, i.e. in spaces 22, is withdrawn through valve 14 which collapses the indwelling catheter except for the balloon 15.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed:

1. A urinary catheter for insertion into a patient, said catheter having a proximal end and a distal end and comprising:
   a) a first substantially collapsible elongated elastomeric tube which is open at the proximal end and closed at the distal end;
   b) a second substantially collapsible elongated elastomeric tube outside of said first tube, said tubes being joined or bonded at said proximal end so as to form an opening into said inner tube and joined and bonded at said distal end, whereby a space is provided between said tubes for insertion of a fluid to stiffen said tubes, said tubes having at least one opening about the distal end for drainage of fluid from the patient into said inner tube;
   c) a valve system for injecting or withdrawing said fluid between said tubes, whereby injection of fluid between said tubes causes stiffening of said catheter and withdrawal of fluid causes collapse of said catheter; and
   d) balloon means about said distal end of said catheter, said balloon means having a valve means separate from the valve system for inserting fluid into said balloon means and inflating said balloon means so as to maintain the catheter within a patient.

2. The catheter of claim 1 including a multiplicity of bonds between said tubes along its length.

3. The catheter of claim 1 wherein said drainage opening and said proximal end is reinforced.

4. The catheter of claim 1 wherein said distal end is thickened.

5. The catheter of claim 1 wherein said tubes comprise latex or silicone rubber.

6. The catheter of claim 1 wherein said drainage opening at the distal end is reinforced to prevent collapse.

7. A collapsible catheter having a proximal end and a distal end comprising:
   a) a first substantially collapsible elongated elastomeric tube having at least one opening at the proximal end and closed at the distal end;
   b) a second substantially collapsible elongated elastomeric tube outside of said first tube; said first and second tubes being bonded and having an opening into the inner at a proximal end and closed at the distal end whereby there is a space between said first and second tube; said first and second tubes having at least one drainage opening near the distal end which is reinforced by a bond between said first and second tubes;
   c) first valve means about said proximal end which permits the insertion of fluid between said tubes so as to stiffen said catheter; and
   d) balloon means about said distal end of said catheter, said balloon means having a second valve means for inserting fluid into said balloon means and inflating said balloon means so as to maintain the catheter within a patient.

8. The catheter of claim 7 wherein said first and second tube are bonded together at a multiplicity of sites.

* * * * *